US011154513B2

(12) United States Patent
Scherer et al.

(10) Patent No.: US 11,154,513 B2
(45) Date of Patent: Oct. 26, 2021

(54) SEMIFLUORINATED COMPOUNDS

(71) Applicant: NOVALIQ GMBH, Heidelberg (DE)

(72) Inventors: Dieter Scherer, Laufen (CH); Ralf Grillenberger, Nuremberg (DE); Frank Löscher, Schriesheim (DE); Hartmut Voss, Schriesheim (DE)

(73) Assignee: NOVALIQ GMBH, Heidelberg (DE)

( * ) Notice: Subject to any disclaimer, the term of this patent is extended or adjusted under 35 U.S.C. 154(b) by 749 days.

(21) Appl. No.: 15/280,411

(22) Filed: Sep. 29, 2016

(65) Prior Publication Data
US 2017/0087101 A1 Mar. 30, 2017

(30) Foreign Application Priority Data

Sep. 30, 2015 (EP) .................................... 15187760
Oct. 30, 2015 (EP) .................................... 15192429

(51) Int. Cl.
*A61K 31/02* (2006.01)
*A61F 9/00* (2006.01)
*A61K 9/00* (2006.01)
*A61K 9/08* (2006.01)
*A61K 47/02* (2006.01)
*C07C 17/266* (2006.01)

(52) U.S. Cl.
CPC ............ *A61K 31/02* (2013.01); *A61F 9/0008* (2013.01); *A61K 9/0048* (2013.01); *A61K 9/08* (2013.01); *A61K 47/02* (2013.01); *C07C 17/266* (2013.01)

(58) Field of Classification Search
None
See application file for complete search history.

(56) References Cited

U.S. PATENT DOCUMENTS

| | | | |
|---|---|---|---|
| 2,616,927 A | 11/1952 | Kauck et al. |
| 5,077,036 A | 12/1991 | Long, Jr. |
| 5,326,566 A | 7/1994 | Parab |
| 5,336,175 A | 8/1994 | Mames |
| 5,518,731 A | 5/1996 | Meadows |
| 5,667,809 A | 9/1997 | Trevino |
| 5,874,469 A | 2/1999 | Maniar et al. |
| 5,874,481 A | 2/1999 | Weers |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch et al. |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,222,292 B2 | 7/2012 | Goskonda et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Wilson |
| 9,757,459 B2 | 9/2017 | Theisinger et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 2002/0004063 A1 | 1/2002 | Zhang |
| 2002/0128527 A1 | 9/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0265362 A1 | 12/2004 | Susilo |

(Continued)

FOREIGN PATENT DOCUMENTS

| | | |
|---|---|---|
| CN | 1147213 A | 4/1997 |
| CN | 200977281 | 11/2007 |

(Continued)

OTHER PUBLICATIONS

Kerns et al., Drug-Like Properties: Concepts, Structure Design and Methods: from ADME to Toxicity Optimization, 2008, Elsevier, Chapter 10, Section 10.4.3, p. 133 (Year: 2008).*
Ahmed, et al., "Disposition of Timolol and Inulin in the Rabbit Eye Following Corneal Versus Non-Corneal Absorption," International Journal of Pharmaceutics, 1987, 38:9-21.
Baerdemaeker, "Pharmacokinetics in Obese Patients," Continuing Education in Anesthesia, Critical Care & Pain, 2004, 4:152-155.
Barata-Vallejo et al., "(Me3Si)3SiH-Mediated Intermolecular Radical Perfluoroalkylation Reactions of Olefins in Water," J. Org. Chem., 2010, 75:6141-6148.

(Continued)

*Primary Examiner* — Jeffrey S Lundgren
*Assistant Examiner* — Tori Strong
(74) *Attorney, Agent, or Firm* — Hoxie & Associates LLC

(57) ABSTRACT

The present invention is directed to certain semifluorinated compounds and to compositions comprising such compounds. The invention further provides the use of the compounds and of the compositions as medicaments for topical administration to the eye.

18 Claims, 2 Drawing Sheets

(56) References Cited

U.S. PATENT DOCUMENTS

| | | |
|---|---|---|
| 2004/0266702 A1 | 12/2004 | Dawson |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153905 A1 | 7/2006 | Carrara et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2009/0149546 A1 | 6/2009 | Chang |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2012/0244177 A1 | 9/2012 | Theisinger et al. |
| 2013/0011484 A1 | 1/2013 | Bevier |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0045282 A1 | 2/2015 | Elsohly et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0182060 A1 | 6/2017 | Wiedersberg et al. |

FOREIGN PATENT DOCUMENTS

| | | |
|---|---|---|
| CN | 202136470 U | 2/2012 |
| CN | 203524843 U | 4/2014 |
| EP | 0 089 815 | 9/1983 |
| EP | 0593552 | 4/1994 |
| EP | 0 670 159 | 9/1995 |
| EP | 0 965 329 | 12/1999 |
| EP | 0 965 334 | 12/1999 |
| EP | 1 152 749 | 11/2001 |
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| JP | 2011/024841 A | 2/2011 |
| WO | WO 1995/033447 | 12/1995 |
| WO | WO 96/40052 | 12/1996 |
| WO | WO 97/12852 | 4/1997 |
| WO | WO 1998/005301 | 12/1998 |
| WO | WO 00/10531 | 3/2000 |
| WO | WO 00/024376 | 5/2000 |
| WO | WO 00/054588 | 9/2000 |
| WO | WO 02/49631 A1 | 6/2002 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/019146 | 2/2008 |
| WO | WO 2008/060359 | 5/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |
| WO | WO 2015/011199 | 1/2015 |
| WO | WO 2015/053829 | 4/2015 |
| WO | WO 2015/074137 | 5/2015 |
| WO | WO 2016/025560 | 2/2016 |
| WO | WO 2016/109531 | 7/2016 |
| WO | WO 2017/220625 | 12/2017 |
| WO | WO 2018/054932 | 3/2018 |
| WO | WO 2018/055101 | 3/2018 |
| WO | WO 2018/060282 | 4/2018 |
| WO | WO 2018/114557 | 6/2018 |
| WO | WO 2018/115097 | 6/2018 |

OTHER PUBLICATIONS

Bardin et al., "Long-Range Nanometer-Scale Organization of Semifluorinated Alkane Monolayers at the Air/Water Interface," Langmuir, 2011, 27:13497-13505.

Blackie et al., "MGD: Getting to the Root Cause of Dry Eye", Review of Optometry, 2012, pp. 1-12.

Broniatowski, M. et al., "Langmuir Monolayers Characteristics of Perfluorodecyl)-Alkanes," Journal of Physical Chemistry B, 2004, 108:13403-13411.

Costa Gomes et al., "Solubility of dioxygen in seven fluorinated liquids," Journal of Fluorine Chemistry, 2004, 125, 1325-1329.

Davies, "Biopharmaceutical Considerations in Topical Ocular Drug Delivery," Clin. Exper. Pharmacol. Physiol., 2000, 27:558-562.

Dembinski et al., Semi-fluorinated Alkanes as Carriers for Drug Targeting in Acute Respiratory Failure, Experimental Lung Research, 2010, 36(8):499-507.

Dias et al., "Solubility of oxygen in liquid perfluorocarbons," Fluid Phase Equilibria, 2004, 222-223:325-330.

English-language machine translation of EP0670159 (A1) issued in U.S. Appl. No. 14/122,025 on Apr. 1, 2015, 10 pages.

Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.

Gayton, J., "Etiology, Prevalence, and Treatment of Dry Eye Disease," Clinical Ophthalmology, 2009, 3:405-412.

Gerdenitsch, "Emulsions—established and promising drug carriers for parenteral administration", retrieved from Internet, date accessed: Jun. 20, 2016, 2 pages URL: <http:/ipimediaworld.com/wp-content/uploads/2012/05/Pages-from-IPI-Volume-2-Issue-1-11.pdf.>.

Gopal et al., "Use of intravitreal injection of triamcinolone acetonide in the treatment of age-related macular degeneration," Indian J Ophthalmol., 2007, 55(6):431-435, (8 pages).

Griffin, W., "Classification of Surface-Active Agnets by 'HLB'," Journal Of The Society of Cosmetic Chemists,1949, 1:311-326.

Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.

(56) References Cited

OTHER PUBLICATIONS

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf et al., "Combined Use of Partially Fluorinated Alkanes, Perfluorocarbon Liquids and Silicone Oil: An Experimental Study," Graefe's Archive For Clinical And Experimental Ophthalmology, 2001, 239(5):373-381.

Holm, R. et al., "A novel excipient, 1-perfluorohexyloctane shows limited utility for the oral delivery of poorly water-soluble drugs," European Journal of Pharmaceutical Sciences, 2011, 42: 416-422.

International Preliminary Report on Patentability dated Apr. 23, 2013, for International Patent Application PCT/EP2011/068141, 4 Pages.

International Preliminary Report on Patentability dated Sep. 18, 2012, for International Patent Application PCT/EP2011/053949, 9 Pages.

International Preliminary Report on Patentability dated May 14, 2013, for International Patent Application PCT/EP2011/069795, 8 Pages.

International Preliminary Report on Patentability dated Jul. 10, 2013, for International Patent Application PCT/EP2012/050043, 5 Pages.

International Preliminary Report on Patentability dated Nov. 26, 2013, for International Patent Application PCT/EP2012/059787, 9 Pages.

International Preliminary Report on Patentability dated Nov. 26, 2013, for International Patent Application PCT/EP2012/059788, 8 Pages.

International Preliminary Report on Patentability dated Jul. 29, 2014, for International Application No. PCT/EP2013/051163, 7 pages.

International Preliminary Report on Patentability dated Mar. 17, 2015, for International Application No. PCT/EP2013/068882, 5 pages.

International Preliminary Report on Patentability dated Mar. 17, 2015, for International Application No. PCT/EP2013/068909, 7 pages.

International Preliminary Report on Patentability dated Jan. 26, 2016, for International Application No. PCT/EP2014/065840, 11 pages.

International Search Report for International Application No. PCT/EP2011/053949 dated Sep. 6, 2011, 5 pages.

International Search Report for International Application No. PCT/EP2011/068141 dated Dec. 14, 2011, 2 pages.

International Search Report for International Patent Application PCT/EP2011/069795 dated Jan. 16, 2012, 3 pages.

International Search Report for International Patent Application PCT/EP2012/050043 dated Apr. 24, 2012, 2 pages.

International Search Report for International Application No. PCT/EP2012/059787 dated Dec. 5, 2012, 4 pages.

International Search Report for International Application No. PCT/EP2012/059788 dated Dec. 3, 2012, 4 pages.

International Search Report for International Application No. PCT/EP2013/051163 dated Mar. 4, 2013, 4 pages.

International Search Report for International Application No. PCT/EP2013/068882 dated Oct. 30, 2013, 4 pages.

International Search Report for International Application No. PCT/EP2013/068909 dated Dec. 5, 2013, 4 pages.

International Search Report for International Application No. PCT/EP2014/065840 dated Oct. 7, 2014, 4 pages.

International Search Report for International Application No. PCT/EP2016/073262 dated Nov. 18, 2016, 5 pages.

International Search Report for International Application No. PCT/EP2016/073263 dated Dec. 23, 2016, 3 pages.

Ishizaki et al., "Treatment of Diabetic Retinopathy", Forum: Complication, Practice, 2009, 26(5): 474-476 (3 pages).

Jonas et al., "Intravitreal triamcinolone acetonide for exudative age-related macular degeneration," Br J Ophthalmol, 2003, 87:462-468.

Joussen et al., "The concept of heavy tamponades—chances and limitations," Graefes Arch Exp Ophthalmol, 2008, 246:1217-1224.

JP 2000511157A, English Machine Translation of the Abstract, Description, and Claims, Espacenet, Date Accessed: Feb. 10, 2016, 15 pages.

JPS6452722, English Machine Translation of the Abstract, Description, and Claims, Espacenet, Date Accessed: Feb. 10, 2016, 4 pages.

Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.

Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.

Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.

Lemp, M., Management of Dry Eye Disease, The American Journal of Managed Care, 2008, 14 (3):S88-S101.

Mackiewicz, J. et al., "In Vivo Retinal Tolerance of Various Heavy Silicone Oils," Investigative Ophthalmology & Visual Science, 2007, 48 (4):1873-1883.

Meinert, H. et al., "Semifluorinated Alkanes—A New Class of Compounds with Outstanding Properties for Use in Ophthalmology," European Journal of Ophthalmology, 2000, 10 (3), 189-197.

Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Opthalmologische Gesellschaft), Poster No. PSa03-02, 1 page (German language version).

Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Opthalmologische Gesellschaft), Poster No. PSa03-02, English Translation, 6 pages.

Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.

Perry, "Dry Eye Disease: Pathophysiology, Classification, and Diagnosis," The American Journal of Managed Care, 2008, 14(3):S79-S87.

Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.

Plassmann, M. et al., "Trace Analytical Methods for Semifluorinated n-Alkanes in Snow, Soil, and Air," Analytical Chemistry, 2010, 82(11):4551-4557.

Plassmann, M. et al., "Theoretical and Experimental Simulation of the Fate of Semifluorinated n-Alkanes During Snowmelt," Environmental Science & Technology, 2010, 44(17):6692-6697.

Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).

Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.

Schnetler et al., "Lipid composition of human meibum: a review," S Afr Optom, 2013, 72(2), 86-93.

Spöler et al., "Towards a New in vitro Model of Dry Eye: The ex vivo Eye Irritation Test", Developments in Ophthalmology, 2010, 45, 93-107.

(56) References Cited

OTHER PUBLICATIONS

Tiffany, J.M., "Individual Variations in Human Meibomian Composition", Exp. Eye Res., 1978, 27, 289-300.
"What is retinal vitrectomy?", Presented by: Medical Online, Obesity and Diabetes Mellitus, 2005, 4(2): 284-286 (3 pages).
Wong et al., "Perfluorocarbons and Semifluorinated Alkanes," Seminars in Ophthalmology; vol. 15 (1), 2000, p. 25-35.
Xalatan, Latanoprost Ophthalmic Solution, 50 µg/mL Prostaglandin $F_{2\alpha}$ analogue, Product Monograph, Jul. 21, 2014, 30 pages.
Zhang et al., "Surface micelles of semifluorinated alkanes in Langmuir-Blodgett monolayers," Phys. Chem. Chem. Phys., 2004, 6:1566-1569.
Chhadva et al., "Meibomian Gland Disease The Role of Gland Dysfunction in Drye Eye Disease," Ophthalmology (2017) 124(11 Supplement): S20-S26.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
Fischer, K.M., et al., "Effects of a topically applied 2% delta-9-tetrahydrocannabinol ophthalmic solution on intraocular pressure and aqueous humor flow rate in clinically normal dogs," American Journal of Veterinary Research, 2013, 74(2):275-280, Abstract Only (2 pages).
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
German, E.J., et al., "Reality of drop size from multi-dose eye drop bottles: is it cause for concern?" Eye, 1999, 13:93-100.
Grotenhermen, F., "Cannabinoids for therapeutic use—Designing systems to increase efficacy and reliability," American Journal of Drug Delivery, 2004, 2(4):229-240, Abstract Only (19 pages).
International Preliminary Report on Patentability dated Dec. 25, 2018, for International Application No. PCT/EP2017/065163, 6 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability dated Apr. 2, 2019, for International Application No. PCT/EP2017/074545, 7 pages.
International Preliminary Report on Patentability dated Jun. 25, 2019, for International Application No. PCT/EP2017/082739, 7 pages.
International Search Report for International Application No. PCT/EP2017/065163, dated Aug. 8, 2017, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/074545 dated Nov. 28, 2017, 3 pages.
International Search Report for International Application No. PCT/EP2017/082739 dated Mar. 6, 2018, 3 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lin, H. et al., "Dry eye disease: A review of diagnostic approaches and treatments," Saudi Journal of Ophthalmology, 2014, 28:173-181.
Matteucci et al., "Biocompatibility assessment of liquid artificial vitreous replacements: relevance of in vitro studies," Survey of Ophthalmology, 2007, 52(3):289-299, Abstract Only (1 page).
Messmer, E.M., "The Pathophysiology, Diagnosis, and Treatment of Dry Eye Disease," (2015) Deutsches Arzteblatt International, 112(5):71-82.
O'Rourke, M. et al., "Enhancing Delivery of Topical Ocular Drops," Cataract & Refractive Surgery Today Europe, 2016, 2 pages.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.
Troiano et al., "Effect of Hypotonic 0.4% Hyaluronic Acid Drops in Dry Eye Patients: A Cross-Over Study," Cornea, 2008, 27(10): 1126-1130, 1 page (Abstract Only).
Wang, W., "Lyophilization and Development of Solid Protein Pharmaceuticals," International Journal of Pharmaceutics, 2000, 203, 1-60.
Wirta, David L. et al., "A Clinical Phase II Study to Assess Efficacy, Safety and Tolerability of Waterfree Cyclosporine Formulation for the Treatment of Dry Eye Disease," Ophthalmology, 2019 126:792-800.
Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).

* cited by examiner

SEMIFLUORINATED COMPOUNDS

CROSS-REFERENCE TO RELATED APPLICATIONS

The present application claims priority to European Patent Application Nos. 15187760.2 filed Sep. 30, 2015, and 15192429.7 filed Oct. 30, 2015, each of which are incorporated by reference in their entireties.

DESCRIPTION

Field

The present invention is in the field of semifluorinated compounds, compositions thereof, and their use as a medicine in particular for ophthalmic administration.

Background

Semifluorinated alkanes are compounds composed of at least one non-fluorinated hydrocarbon segment and at least one perfluorinated hydrocarbon segment. Linear, unbranched semifluorinated alkanes of the general formula $CF_3(CF_2)_n(CH_2)_mCH$, wherein n and m are integers denoting the number of carbon atoms of the respective segment are described for various applications, for example commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery.

Semifluorinated alkanes of the formula $CF_3(CF_2)_n(CH_2)_mCH_3$ are described in other applications.

WO 2011/073134 discloses solutions of ciclosporin in a semifluorinated alkanes of the formula $CF_3(CF_2)_n(CH_2)_mCH_3$, optionally in the presence of a co-solvent such as ethanol, wherein the semifluorinated alkane functions as a liquid drug delivery vehicle for ciclosporin for topical treatment of keratoconjunctivitis sicca.

WO2014/041055 describes mixtures of semifluorinated alkanes of the formula $CF_3(CF_2)_n(CH_2)_mCH_3$ (which may be alternatively expressed as $F(CF_2)_n(CH_2)_mH$). These mixtures are described to be ophthalmically applicable as tear film substitutes or for treating patients with dry eye syndrome and/or meibomian gland dysfunction.

A nomenclature which is frequently used for semifluorinated compounds having linear and unbranched segments is FnHm, wherein F means a perfluorinated hydrocarbon segment, H means a non-fluorinated segment, and n and m define the number of carbon atoms of the respective segment. For example, F3H3 is used for perfluoropropylpropane, $CF_3(CF_2)_2(CH_2)_2CH_3$, i.e. 1-perfluoropropylpropane.

Semifluorinated alkanes of the general formula $CF_3—(CF_2)_n—CH(CH_3)—(CH_2)_m—CH_3$ however have not been described, in particular for ophthalmic applications. It is therefore an object of the invention to provide such compounds, in particular in respect of their use in compositions, especially with utility in the field of ophthalmic applications.

SUMMARY OF THE INVENTION

In a first aspect, the invention relates to compositions comprising a semifluorinated compound characterized by the general formula $CF_3—(CF_2)_n—CH(CH_3)—(CH_2)_m—CH_3$ wherein n is an integer selected from 3 to 5 and m is an integer selected from 1 to 5. Preferably, these compositions are in the form of a liquid, wherein the compositions comprise at least 1 wt. %, in particular from 1 wt. % to 5 wt. % of a compound characterized by $CF_3—(CF_2)_n—CH(CH_3)—(CH_2)_m—CH_3$ wherein n is an integer selected from 3 to 5 and m is an integer selected from 1 to 5.

In another aspect, the present invention relates to compositions comprising said compounds in the form of clear, liquid solutions, and also compositions which essentially consist of said compounds and optionally one or more lipophilic liquid constituents.

In still another aspect, the invention provides the use of compositions comprising said compounds for treatment of dry eye disease and/or Meibomian Gland Dysfunction and any symptoms or conditions associated therewith.

In a further aspect, the present invention provides a method for treatment of dry eye disease and any symptoms or conditions associated therewith, comprising administering said composition topically to the lacrimal sac, into the lower eyelid, to an eye surface or to an ophthalmic tissue.

In a yet further aspect, the present invention provides a kit comprising compositions of the present invention held in a container which comprises dispensing means adapted for topical administration of the composition to the eye or ophthalmic tissue.

DETAILED DESCRIPTION OF THE INVENTION

Figure 1:
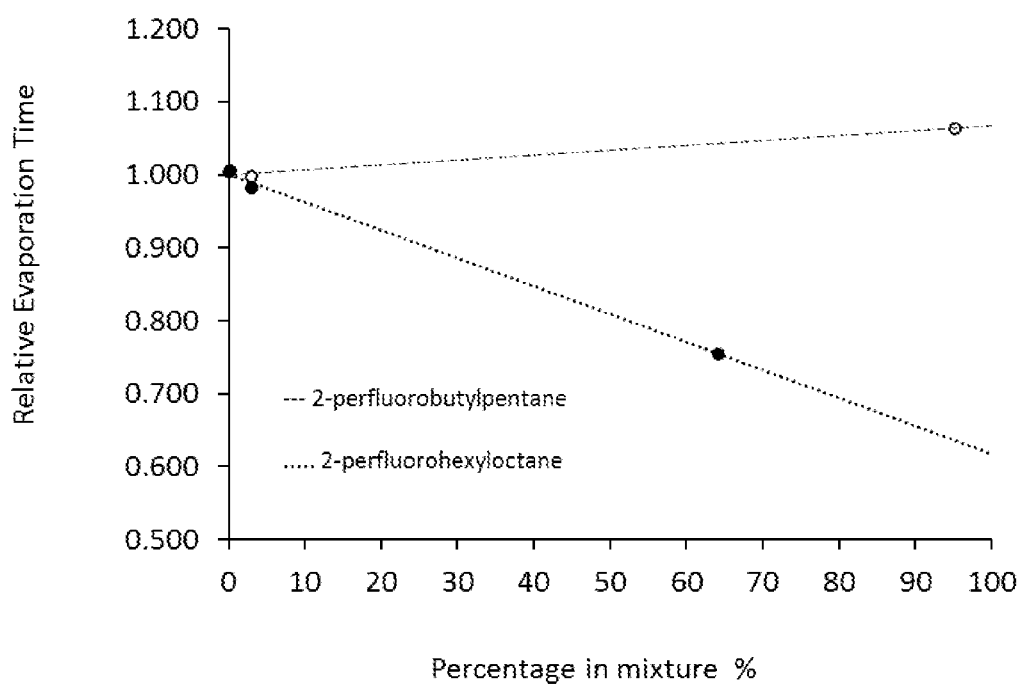
FIG. 1 is a graph depicting the relative evaporation time of compositions consisting of the compounds $CF_3(CF_2)_5(CH_2)_7CH_3$ and $CF_3—(CF_2)_5—CH(CH_3)—(CH_2)_5—CH_3$ as a function of the percentage of the latter compound in the composition (indicated by the solid circle and dotted line in the graph), and the relative evaporation time of compositions consisting of the compounds $CF_3(CF_2)_3(CH_2)_4CH_3$ and $CF_3—(CF_2)_3—CH(CH_3)—(CH_2)_2—CH_3$ as a function of the percentage of the latter compound in the composition (indicated by the transparent circle and dashed line in the graph).

In a first aspect, the invention relates to a semifluorinated compound characterized by the general formula $CF_3—(CF_2)_n—CH(CH_3)—(CH_2)_m—CH_3$ wherein n is an integer selected from 3 to 5 and m is an integer selected from 1 to 5.

Particularly preferred compounds of the formula $CF_3—(CF_2)_n—CH(CH_3)—(CH_2)_m—CH_3$ are those in which n is 5 and m is 5 (i.e. formula $CF_3—(CF_2)_5—CH(CH_3)—(CH_2)_5—CH_3$), or wherein n is 3 or and m is 2 (i.e. formula $CF_3$—$(CF_2)_3$—$CH(CH_3)$—$(CH_2)_2$—$CH_3$). Other preferred compounds include $CF_3$—$(CF_2)_3$—$CH(CH_3)$—$(CH_2)_3$—$CH_3$, $CF_3$—$(CF_2)_3$—$CH(CH_3)$—$(CH_2)_5$—$CH_3$, $CF_3$—$(CF_2)_5$—$CH(CH_3)$—$(CH_2)_1$—$CH_3$, and $CF_3$—$(CF_2)_5$—$CH(CH_3)$—$(CH_2)_3$—$CH_3$.

Alternatively, the compounds of the invention may be also generally be referred to as 2-perfluoroalkylalkanes, for instance, the compound $CF_3$—$(CF_2)_5$—$CH(CH_3)$—$(CH_2)_5$—$CH_3$ may also be referred to as 2-perfluorohexyloctane, based on the hydrocarbon alkane as the root.

The compounds feature a stereocenter at the 2-alkyl position. As understood herein, the general formula encompasses both enantiomers, enriched mixtures of the two enantiomers, as well as the racemic mixture.

It has been found that compounds as defined above provide a number of unexpected advantages, as outlined below. They are particularly useful when provided as compositions such as for medical applications, in particular for topical administration, such as topical ophthalmic administration.

The present invention relates to compositions comprising these semifluorinated compound characterized by the general formula $CF_3$—$(CF_2)_n$—$CH(CH_3)$—$(CH_2)_m$—$CH_3$ as defined above are preferably in the liquid form, for example formulated to be administered as a liquid solution. In optional embodiments, the compositions may be formulated to be administered as a gel, suspension, microemulsion, or a spray. Preferably, the compositions are provided in sterile form.

In a particularly preferred embodiment, compositions comprising a semifluorinated compound characterized by the general formula $CF_3$—$(CF_2)_n$—$CH(CH_3)$—$(CH_2)_m$—$CH_3$ wherein n is an integer selected from 3 to 5 and m is an integer selected from 1 to 5 is in a liquid form and comprises at least 1 wt. % of the compound, in particular from 1 wt. % to 5 wt. %, based on the total weight of the composition. In other embodiments, the composition may comprise between about 3 wt. % to 5 wt. %, or about 5 wt. % to 10 wt. %, or up to 25 wt. % of the compound based on the total weight of the composition.

In one of the preferred embodiments, the composition as defined above is formulated as a clear, liquid solution. In this context, clear means the absence of dispersed solid or liquid particles which cause turbidity. In other words, such clear solution is a purely monophasic liquid system, except that minor and technically irrelevant amounts of particulate impurities may be present.

Moreover, the composition is preferably formulated as a liquid solution which exhibits a refractive index that is close to that of water which is 1.333 at room temperature (RT). In a particularly preferred embodiment, the refractive index of the liquid solution is in the range of from about 1.30 to about 1.35 at 20° C., as determined by refractometer.

The compositions as defined above may also comprise further excipients as required or as useful, such as one or more acids, bases, electrolytes, buffers, solutes, antioxidants, stabilizers, and if required, preservatives. In one preferred embodiment, the compositions as defined above are substantially free of water and/or substantially free of a preservative, such as benzalkonium chloride.

In another preferred embodiment, the composition of the invention is formulated as clear liquid solution that is substantially free of the following: (a) a polymer (b) a perfluorinated compound, and/or (c) a dissolved pharmacologically active ingredient which is not a semifluorinated alkane. In another embodiment, the composition as described herein may be substantially free of a pharmacologically active ingredient in any form and which is not a semifluorinated alkane.

As understood herein, the term 'substantially free' in reference to a composition constituent refers to the presence of said constituent in no more than trace amounts and that if present in trace amounts the constituent provides no technical contribution to the composition.

Examples of polymers which are preferably absent in the compositions of the invention include silicone polymers (polymerized siloxanes), polyether polymers and fluorinated or perfluorinated derivatives thereof.

Examples of perfluorinated compounds, i.e. compounds in which all the hydrogen atoms are replaced with fluorine, and which are preferably absent in the compositions of the invention include perfluoroalkanes such as perfluorodecalin, as well as halogenated perfluoroalkanes such as perfluorooctylbromide.

The compositions of the invention that are in the form of a clear liquid solution are also substantially free of a dissolved pharmacological active ingredient which is not a semifluorinated alkane. As used herein, the term "pharmacological active ingredient" refers to any type of pharmaceutically active compound or drug, i.e. one that produces a pharmacological effect and that may accordingly be useful in the prevention, diagnosis, stabilization, treatment, or generally speaking, the management of a condition or disease.

The compounds of the invention as well as the compositions comprising these, even if free of other pharmacologically active ingredients, however have beneficial therapeutic effects at the site of administration.

In a further preferred embodiment, the compositions of the invention essentially consist of a compound characterized by the general formula $CF_3$—$(CF_2)_n$—$CH(CH_3)$—$(CH_2)_m$—$CH_3$ wherein n is an integer selected from 3 to 5 and m is an integer selected from 1 to 5, and optionally, one or more lipophilic liquid constituents. In a particular embodiment, the composition consists essentially of either the compound $CF_3$—$(CF_2)_5$—$CH(CH_3)$—$(CH_2)_5$—$CH_3$ or $CF_3$—$(CF_2)_3$—$CH(CH_3)$—$(CH_2)_2$—$CH_3$, or a mixture thereof, and optionally one or more lipophilic liquid constituents.

As used herein, the term "essentially consisting of" is so-called closed language, meaning that only the mentioned constituents are present. In contrast, the terms "comprise", "comprises" and "comprising" are used herein as so-called open language, meaning that further constituents may also be present.

The optional lipophilic liquid constituents are preferably substantially non-water soluble and/or non-water miscible excipients, for example oily excipients such as lipids, triglyceride oils and any other oils that are physiologically tolerated by the eye, or other semifluorinated alkanes such as in the class belonging to the general formula $CF_3(CF_2)_n(CH_2)_mCH_3$, wherein n and m are integers independently selected from the range of 3 to 8, for example, $CF_3(CF_2)_3(CH_2)_4CH_3$ or $CF_3(CF_2)_5(CH_2)_7CH_3$.

Such lipophilic liquid constituents may be present in the composition in amounts up to about 25 wt. % or up to about 50 wt. %, or 75 wt. % or 90 wt. %, 95 wt. % or 97 wt. % of the composition, based on total weight of the composition.

In a further preferred embodiment, the composition according to the present invention comprises or essentially consists of $CF_3$—$(CF_2)_5$—$CH(CH_3)$—$(CH_2)_5$—$CH_3$ and $CF_3$—$(CF_2)_5$—$(CH_2)_7$—$CH_3$; or of $CF_3$—$(CF_2)_3$—CH($CH_3$)—$(CH_2)_2$—$CH_3$ and $CF_3$—$(CF_2)_3$—$(CH_2)_4$—$CH_3$ The compositions as defined above are preferably formulated to have a dynamic viscosity of not more than 10 mPa·s, and preferably not more than 4 mPa·s, as determined under standard ambient temperature and pressure (25° C., 1 atm). Preferably, the compositions have a dynamic viscosity of between 1 and 4 mPa·s. The viscosity of the compositions may be determined using any standard viscometer device known in the art, such as a glass tube or capillary viscometer.

The compounds characterized by the general formula $CF_3$—$(CF_2)_n$—$CH(CH_3)$—$(CH_2)_m$—$CH_3$ wherein n is an integer selected from 3 to 5 and m is an integer selected from 1 to 5 and compositions thereof as described herein may be used in medical applications, in particular for use in ophthalmology, in particular in the topical administration to the eye, such as to the lacrimal sac, into the lower eyelid, to an eye surface or to any ophthalmic tissue or anatomy associated with the eye that may be made available for topical administration.

In particular, the compounds of the invention are beneficial for use in the treatment of diseases and conditions which would benefit from stabilization of the tear film and tear film lipid layer and lubrication of the eye surface. Thus, the compositions of the present invention are especially suited in the treatment of dry eye disease (keratoconjunctivitis sicca) and/or Meibomian Gland Dysfunction (MGD) and any symptoms thereof or associated therewith.

Dry eye disease, also known as keratoconjunctivitis sicca, can be distinguished into two categories, namely aqueous deficient dry eye disease and evaporative dry eye disease. These conditions are not necessarily mutually exclusive. Aqueous deficient dry eye is typically observed in patients suffering from Sjö gren syndrome, or those suffering from a lacrimal gland insufficiency, lacrimal duct obstruction or reflex hyposecretion. Evaporative dry eye disease on the other hand has diverse root causes and is associated with increased/abnormal evaporative loss of the tear film, for example as a result of meibomian gland disorders, eyelid aperture disorders, blinking disorders, or ocular surface disorders.

Symptoms of dry eye disease include dry, scratchy, gritty, sandy or foreign body sensations in the eye; pain, soreness, stinging or burning; itching, increased need for blinking, eye fatigue, photophobia, blurry vision, redness and inflammation of the eye tissue, excess mucus discharge and crusting/clotting, contact lens intolerance, and excess reflex tearing.

Meibomian Gland Dysfunction (MGD) refers to a condition where the meibomian glands do not secrete enough oil, or when the oily secretion is of poor or abnormal quality. Often, the oil gland openings may become plugged up and obstructed so that less oil is secreted from the glands. The oil that is secreted from the glands can be granular (crusty) or otherwise abnormal, and can cause irritation to the eye. In the early stages, patients are often asymptomatic, but if left untreated, MGD can cause or exacerbate dry eye symptoms and eyelid inflammation. The oil glands become blocked with thickened secretions. Chronically clogged glands eventually become unable to secrete oil, which may result in permanent changes in the tear film and dry eyes.

Symptoms of Meibomian Gland Dysfunction include dryness, burning, itching, stickiness/crustiness, watering, light sensitivity, red eyes, foreign body sensation, chalazion/styes or intermittent blurry vision.

In a preferred embodiment of the invention, the compounds and compositions thereof as described above are used for the topical ophthalmic treatment of evaporative dry eye disease and/or Meibomian Gland Dysfunction, and relief of any one of the symptoms associated therewith.

In one embodiment of the invention, the ophthalmic composition comprising of a semifluorinated compound characterized by the general formula $CF_3$—$(CF_2)_n$—$CH(CH_3)$—$(CH_2)_m$—$CH_3$ wherein n is an integer selected from 3 to 5 and m is an integer selected from 1 to 5; or preferably, wherein n is 5 and m is 5 (i.e. formula $CF_3$—$(CF_2)_5$—$CH(CH_3)$—$(CH_2)_5$—$CH_3$), or wherein n is 3 or and m is 2 (i.e. formula $CF_3$—$(CF_2)_3$—$CH(CH_3)$—$(CH_2)_2$—$CH_3$), are used for the treatment of dry eye disease (keratoconjunctivitis sicca) or a symptom associated therewith. In another embodiment, such composition may be used for the treatment of Meibomian Gland Dysfunction or a symptom associated therewith.

In further embodiments, the treatment of these conditions is preferably carried out by a method of administering to a patient in need thereof, an effective amount of a composition essentially consisting of said semifluorinated alkane, and optionally one or more lipophilic liquid constituents that are preferably substantially non-water soluble and/or non-water miscible excipients, for example oily excipient such as lipids, triglyceride oils and any other oils that are physiologically tolerated by the eye, or other semifluorinated alkanes such as in the class belonging to the general formula $CF_3(CF_2)_n(CH_2)_mCH_3$, wherein n and m are integers independently selected from the range of 3 to 8, for example, $CF_3(CF_2)_3(CH_2)_4CH_3$ or $CF_3(CF_2)_5(CH_2)_7CH_3$.

In a further preferred embodiment of the invention, the compounds and compositions thereof as described above are used for the topical ophthalmic treatment of corneal damage. Thus, said compounds and compositions are actively supporting the corneal healing process of corneal damage, such as corneal erosions.

The advantages of the compounds described above in the context of their use according to the present invention are believed to relate to their properties which are particularly suited for ophthalmic applications. The close proximity of the refractive indices of the compounds of the invention to that of water, means that there would be no or minimal impact of a patient's vision subsequent to administration, unlike ophthalmic compositions based on oily carriers which can confer blurry vision on administration. The generally low viscosity and low surface tension and in particular their high wetting and spreading capabilities of these compounds also ensures that they are rapidly accommodated and adapted on administration over the surface of the eye.

As will be made clearer in the examples below, it was found that the compounds and compositions thereof are biocompatible and exhibit no apparent cytotoxic effects. Moreover, it has been established that said compounds and their compositions are not only well tolerated in the eye, but also provide a beneficial effect in terms of lubrication of the eye and stabilization of the tear film, in the form of relief in symptoms of patients having mild to moderate symptoms associated with dry eye disease and/or Meibomian Gland Dysfunction. Patients with dry eye disease and/or dysfunctional meibomian glands often express opaque and thicker meibum which can lead to an abnormal lipid layer in the tear film. Without wishing to be bound to theory, it is believed that the physico-chemical attributes of the compounds of the invention may play a role in stabilizing the lipid layer of the tear film, such as by solubilization of certain lipid components or improving the fluidity of the lipid layer.

In a further aspect, the present invention provides a method for treatment of dry eye disease and any symptoms or conditions associated thereof comprising administering the compositions of the present invention topically to the lacrimal sac, into the lower eyelid, to an eye surface or to an ophthalmic tissue. Preferably, said compositions can be administered to the eye or eye tissue up to four times per day.

Furthermore, the invention provides a kit comprising any one of the compositions as described above, and a container for holding said composition. Said container preferably comprises a dispensing means adapted for topical administration of the composition to an eye sac, lower eyelid to an eye or ophthalmic tissue, such as an eye dropper.

In a further preferred embodiment, the dispensing means comprises a dropper of dimensions such as to dispense droplets having a volume of about 8 to 15 μL, preferably having a volume of about 8-12 μl, more preferably having a volume of about 10 μl. With a small droplet volume, precise dosing to the eye can be achieved and an excess amount of discharge of a substantial fraction of the composition from the eye subsequent to administration can be avoided.

EXAMPLES

Preparation of $CF_3-(CF_2)_5-CH(CH_3)-(CH_2)_5-CH_3$ (2-Perfluorohexyl-octane, $C_{14}F_{13}H_{17}$)

The compound $CF_3-(CF_2)_5-CH(CH_3)-(CH_2)_5-CH_3$ may be prepared as follows: radical addition of perfluorohexyl iodide with 1-octene in the presence of a radical initiator (herein perfluorohexyl iodide is mixed with 1-octene and a radical initiator as AIBN and the obtained solution is maintained at 80° C. for 30 min and cooled down), followed by reduction of the resulting iodo adduct with hydride (i.e. $LiALH_4$) or via hydrogenation (i.e. catalytic hydrogenation in presence of a catalyst such as Pd/C) to form 2-perfluorohexyl-octane, followed by purification by fractional distillation. Other compounds of formula $CF_3-(CF_2)_n-CH(CH_3)-(CH_2)_m-CH_3$ as defined above may be prepared analogously by this general method.

$CF_3-(CF_2)_5-CH(CH_3)-(CH_2)_5-CH_3$: $^1$H-NMR ($CDCl_3$, 400 MHz): 2.17-2.33 (m, 1H, CH), 1.67-1.77 (m, 2H, $CH_2$), 1.25-1.40 (m, 8H, $CH_2$), 1.15 (d, 3H, $CH_3$), 0.90 (t, 3H, $CH_3$).

Preparation of $CF_3-(CF_2)_3-CH(CH_3)-(CH_2)_2-CH_3$ (2-Perfluorobutyl-pentane, $C_9F_9H_{11}$)

The compound $CF_3-(CF_2)_3-CH(CH_3)-(CH_2)_2-CH_3$ may be prepared according to the general method described above with perfluorobutyl iodide and 1-pentene as the starting materials.

$CF_3-(CF_2)_3-CH(CH_3)-(CH_2)_2-CH_3$: $^1$H-NMR ($CDCl_3$, 400 MHz): 2.21-2.32 (m, 1H, CH), 1.68-1.74 (m, 2H, $CH_2$), 1.45-1.55 (m, 2H, $CH_2$), 1.12 (d, 3H, $CH_3$), 0.92 (t, 3H, $CH_3$).

In Vitro Cytotoxicity Assay

The cytotoxicity of a composition comprising 1.3 wt. % $CF_3-(CF_2)_5-CH(CH_3)-(CH_2)_5-CH_3$ and 95.8 wt. % $CF_3(CF_2)_5(CH_2)_7CH_3$ was assessed by a cell growth inhibition test which predicts cytotoxic or necrotic effects with good correlation to animal experiments and high sensitivity. The composition was extracted by cell culture medium (DMEM supplemented with 10% FBS) under agitation for ~24 hours. The resulting extract was then incubated with mouse cell line L929 cells for 68-72 hours, before the protein content was analyzed using a BCA (bicinchoninic acid) test as a measure for cytotoxicity. No inhibition of cell growth or cell lysis was observed.

An analogous in vitro cytotoxicity assay is conducted for a composition comprising about 23.7 wt. % $CF_3-(CF_2)_5-CH(CH_3)-(CH_2)_5-CH_3$ and about 75.6 wt. % F6H8.

Tear Film Analysis Studies

A composition comprising 98.3 wt. % of $CF_3(CF_2)_5(CH_2)_7CH_3$ and 1.2 wt. % of $CF_3-(CF_2)_5-CH(CH_3)-(CH_2)_5-CH_3$ was tested in an observational study in patients with mild to moderate evaporative dry eye disease. The clear colorless liquid composition was provided in a 5 ml bottle equipped with a dropper dimensioned to dispense droplets of ~10 μl per drop into the eye sac. Patients wearing contact lenses were excluded from the study. After informed consent had been obtained, patients were advised to apply 3-4 drops, daily in both eyes, translating to a daily dose of 30-40 μl. Patients returned after 5-7 weeks for follow-up. Clinical data for 29 patients were collected at baseline and at the 5-7 week follow-up visit.

a) Tear Film Analysis

Tear film fluid and tear film stability improved over the study period, as can be seen in the increase in Schirmer I and the TFBUT. The retrospective statistical analysis is strengthening this observation, as the difference in TFBUT at baseline and follow-up is highly significant (paired two-sided t-test: p=0.0026 (right eyes) and p=0.0006 (left eyes)). No changes were detected in tear osmolarity.

The subjective dry eye questionnaire (Ocular Surface Disease Index, OSDI) revealed that patient's subjective symptom severity decreased after the use of the composition comprising 98.3 wt. % of $CF_3(CF_2)_5(CH_2)_7CH_3$ and 1.2 wt. % of $CF_3-(CF_2)_5-CH(CH_3)-(CH_2)_5-CH_3$ over a 5-7 week period, as can be seen in the lower scores at follow-up and the retrospective statistical analysis (paired two sided t-test: p<0.0001).

| Parameter | Baseline | Follow up |
|---|---|---|
| Schirmer I (mm/5 min)/ Right eye | 10.7 + 3.7 | 16.3 + 8.9 |
| TFBUT (sec) | Right eye: 5.7 + 2.6 Left eye: 5.7 + 2.6 | Right eye: 7.9 + 5.1 Left eye: 8.6 + 6.0 |
| Osmolarity | 315.7 + 12.8 | 311.4 + 14.7 |
| OSDI | 53.9 + 22.5 | 35.8 + 22.9 | b) Corneal Staining (Oxford Grading Scheme)

Corneal fluorescein staining is an indicator of corneal damage (loss of cell-to-cell junctions). The data indicate a reduction of corneal damage after 5-7 weeks of treatment, as can be seen in the shift of numbers of patients diagnosed with Grade 1 or 2 at baseline towards Grade 0 at follow-up. This difference to the initial level of damage was statistically significant, as shown by Wilcoxon signed rank test: p=0.0013 (right eyes) and p=0.0041 (left eyes).

| | Baseline (n = 29) | | | Follow up (n = 28) | | |
|---|---|---|---|---|---|---|
| | Grade 0 | Grade 1 | Grade 2 | Grade 0 | Grade 1 | Grade 2 |
| Right eye (n) | 8 (1) | 16 | 4 | 25 | 2 | 1 |
| Left eye (n) | 8 (1) | 16 | 4 | 19 | 9 | 0 | c) Symptom Assessment by Physician

Patients were asked by the physician whether they currently suffer from typical dry eye symptoms both at the baseline and at the follow-up visit. As can be seen in the table below, a lower number of DED-associated symptoms were reported after 5-7 weeks of treatment.

|  | Baseline | Follow up |
|---|---|---|
| Red eyes | 25 | 9 |
| Itching | 21 | 10 |
| Clotted eyes | 9 | 2 |
| Stringy mucous | 4 | 1 |
| Headache | 2 | 1 | d) Meibum Secretion Analysis

In a healthy eye, meibum is secreted from the meibomian glands as a clear liquid. More opaque and thicker meibum is an indicator of dysfunctioning meibomian glands. Patients' meibum was descriptively examined at both the baseline and the follow-up visit. According to the data obtained, meibum quality improved in a number of cases. In seven cases, the treatment induced a reduction of expressible meibum (changing from clear meibum to none).

|  | Baseline | Follow up |
|---|---|---|
| Clear | 20 | 17 |
| Whitish | 6 | 3 |
| Thick | 1 | 0 |
| None | 2 | 9 | e) Safety Parameters

No changes were seen in either visual acuity or intraocular pressure, indicating that the use of composition comprising 98.3 wt. % of $CF_3(CF_2)_5(CH_2)_7CH_3$ and 1.2 wt. % of $CF_3$—$(CF_2)_5$—$CH(CH_3)$—$(CH_2)_5$—$CH_3$ over 5-7 weeks is safe and does not interfere with these ophthalmological parameters.

|  | Baseline | Follow up |
|---|---|---|
| Visual acuity | 0.8 (0.7-1.0) | 0.9 (0.8-1.0) |
| Intraocular pressure (mm HG) | 14.9 ± 2.6 | 14.6 ± 3.2 |

Differential Scanning Calorimetry

Differential Scanning Calorimetry (DSC 1, Mettler Toledo, Greifensee, Switzerland) is used to characterize structure and phase behavior of mixtures of $CF_3(CF_2)_5$—$CH(CH_3)$—$(CH_2)_5$—$CH_3$ and $CF_3(CF_2)_5(CH_2)_7CH_3$. DSC was employed to obtain data on transitions by temperature rising scans with heating rate of 1° C./min. Sealed standard aluminum crucibles (40 μl, Mettler Toledo) were used.

| wt % $CF_3$—$(CF_2)_5$—$CH(CH_3)$—$(CH_2)_5$—$CH_3$ | Melting transition | | | |
|---|---|---|---|---|
|  | ΔH (J/g) | Onset (° C.) | Peak (° C.) | Endset (° C.) |
| 0 | −36.57 | −6.33 | −4.53 | −2.14 |
| 5.91 | −33.36 | −10.32 | −7.99 | −7.24 |
| 12.03 | −29.42 | −13.74 | −10.44 | −9.58 |
| 23.74 | −24.09 | −21.56 | −15.38 | −14.17 |

| wt % $CF_3(CF_2)_5$—$CH(CH_3)$—$(CH_2)_5$—$CH_3$ | Low temperature transition | | | |
|---|---|---|---|---|
|  | ΔH (J/g) | Onset (° C.) | Peak (° C.) | Endset (° C.) |
| 0 | −0.69 | −45.47 | −40.37 | −38.32 |
| 5.91 | −0.56 | −50.61 | −45.77 | −42.93 |
| 12.03 | −0.44 | −55.18 | −48.58 | −45.53 |
| 23.74 | −0.19 | −60.75 | −54.39 | −52 |

The presence of $CF_3(CF_2)_5$—$CH(CH_3)$—$(CH_2)_5$—$CH_3$ in a mixture of $CF_3(CF_2)_5$—$(CH_2)_7$—$CH_3$(F6H8) resulted in a significant reduction in the melting temperature. The melting enthalpy is also decreased, which suggests that this semifluorinated alkane does not crystallize. Such differences will have a beneficial effect in respect of the application of this compound to the eye as a tear film substitute or lubricant; for example, in terms of its ability to mix with, and to modulate the tear film lipid layer. Such effects can moreover be advantageously tuned by varying the amounts of the compound which are added to ophthalmic compositions.

DSC measurements of a series of mixtures of 23.74 wt. % of $CF_3(CF_2)_5$—$CH(CH_3)$—$(CH_2)_5$—$CH_3$ and $CF_3(CF_2)_5(CH_2)_7CH_3$ with tetradecane (C14) was also performed. Data on transitions were obtained with temperature rising scans (heating rates 0.2, 0.5 and 1° C./min). Extrapolation to a heating rate of 0° C./min was used to determine endset temperatures while average from the three measurements were used to determine onset temperatures. A decrease in the melting enthalpy was observed, compared to mixtures of tetradecane with pure $CF_3(CF_2)_5(CH_2)_7CH_3$, suggesting that some of the tetradecane is dissolved in the liquid fraction of $CF_3(CF_2)_5$—$CH(CH_3)$—$(CH_2)_5$—$CH_3$ and that this compound has a stronger solubilizing capacity compared to $CF_3(CF_2)_5(CH_2)_7CH_3$.

Refractive Index and Evaporation Time

The evaporation time of mixtures of the semifluorinated alkane $CF_3(CF_2)_3(CH_2)_4CH_3$(F4H5) and $CF_3$—$(CF_2)_3$—$CH(CH_3)$—$(CH_2)_2$—$CH_3$ was evaluated. A droplet of 10 μL volume of each mixture was placed on a glass surface at room temperature. Time until evaporation was recorded by video-monitoring.

| Sample | $CF_3(CF_2)_3(CH_2)_4CH_3$/% | $CF_3$—$(CF_2)_3$—$CH(CH_3)$—$(CH_2)_2$—$CH_3$/% | Evaporation time/s | Relative Evaporation Time |
|---|---|---|---|---|
| 1 | 99.95 | 0.00 | 304 | 1.00 |
| 2 | 96.85 | 2.99 | 302 | 0.998 |
| 3 | 0.00 | 95.13 | 322 | 1.064 |

It was observed that an increased amount of the compound $CF_3$—$(CF_2)_3$—$CH(CH_3)$—$(CH_2)_2$—$CH_3$ appears to increase the evaporation time of the mixture (see FIG. 1).

The evaporation time of mixtures of the semifluorinated alkane $CF_3(CF_2)_5(CH_2)_7CH_3$(F6H8) and $CF_3(CF_2)_5$—$CH(CH_3)$—$(CH_2)_5$—$CH_3$ was evaluated analogously.

| Sample | $CF_3(CF_2)_5(CH_2)_7CH_3$/% | $CF_3(CF_2)_5$—$CH(CH_3)$—$(CH_2)_5$—$CH_3$/% | Evaporation time/s | Relative Evaporation Time |
|---|---|---|---|---|
| 1 | 99.84 | 0.16 | 13260 | 1 |
| 2 | 96.53 | 3.05 | 12960 | 0.97 |
| 3 | 26.3 | 64.1 | 9960 | 0.75 |

In contrast, it was unexpectedly observed that an increasing percentage of the semifluorinated alkane $CF_3(CF_2)_5$—$CH(CH_3)$—$(CH_2)_5$—$CH_3$ significantly decreases the evaporation time of the mixtures (see FIG. 1).

Thus, depending on the compound characterized by the general formula $CF_3$—$(CF_2)_n$—$CH(CH_3)$—$(CH_2)_m$—$CH_3$ wherein n is an integer selected from 3 to 5 and m is an integer selected from 1 to 5 and amount present in the mixture, it may feasible to adapt and fine-tune the composition to the requirements of the intended ophthalmic use, such as in terms of prolonging or reducing the residence time of the composition on the eye surface.

Figure 2:
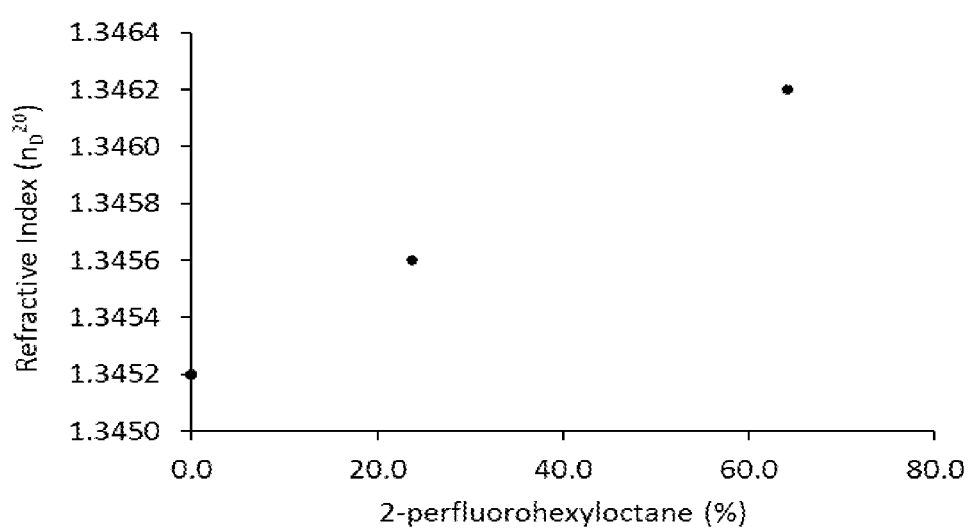
FIG. 2 is a graph depicting the refractive index determined for compositions consisting of the compounds $CF_3(CF_2)_5(CH_2)_7CH_3$ and $CF_3—(CF_2)_5—CH(CH_3)—(CH_2)_5—CH_3$ as a function of the percentage of the latter compound in the composition.
Figure 3:
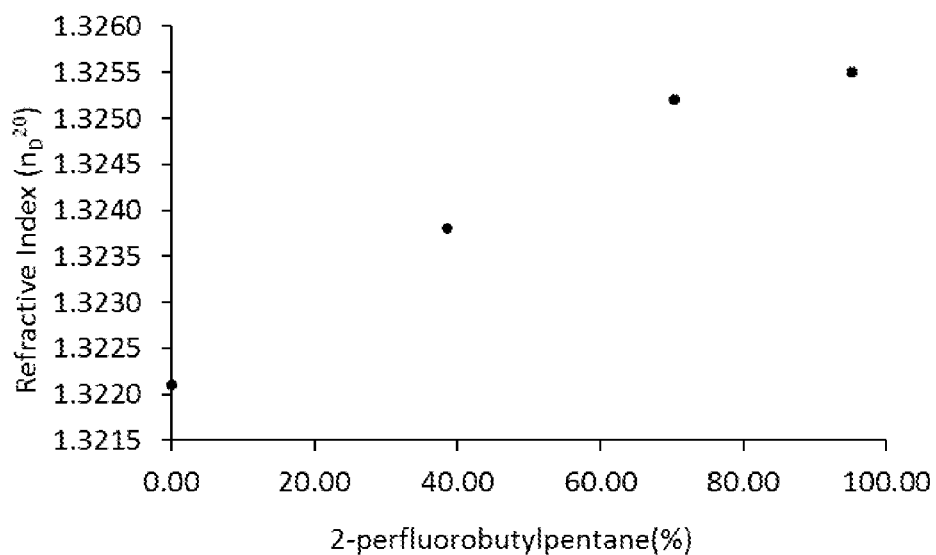
FIG. 3 is a graph depicting the refractive index determined for compositions consisting of the compounds $CF_3(CF_2)_3(CH_2)_4CH_3$ and $CF_3—(CF_2)_3—CH(CH_3)—(CH_2)_2—CH_3$ as a function of the percentage of the latter compound in the composition.
Figure 4:
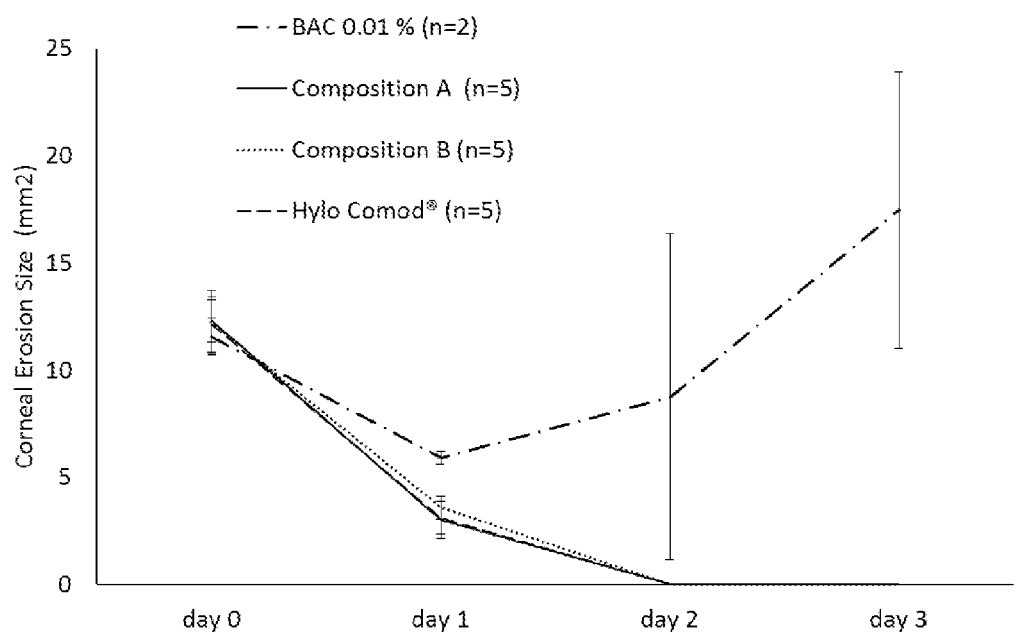
FIG. 4 is a graph representing the corneal erosion size measurements ($mm^2$) over the course of three days of an Ex vivo Eye Irritation Test (EVEIT) comparison of compositions comprising $CF_3(CF_2)_5(CH_2)_7CH_3$ and $CF_3—(CF_2)_5—CH(CH_3)—(CH_2)_5—CH_3$, a hyaluronic standard reference and 0.01% BAC positive control.

The refractive index of the mixtures was also determined. For topically applied ophthalmic compositions, the refractive index of the composition should preferably be similar, or adapted to that of the eye and lens, for instance as close to that of physiological tear fluid as possible. If the refractive index of a composition is not similar, when applied to the surface of the eye, a patient may experience blurring or impaired vision. It is observed, that the amount of the compound $CF_3(CF_2)_5$—$CH(CH_3)$—$(CH_2)_5$—$CH_3$ or has an effect on refractive index. FIG. 2 depicts an increasing refractive index value with increased content of the 2-perfluorohexyl-octane in a mixture with 1-perfluorohexyl-octane. FIG. 3 likewise depicts an increasing refractive index value with increasing content of 2-perfluorobutyl-pentane in a mixture with 1-perfluorobutylpentane.

By varying the amount of these compounds, such as characterized by the general formula $CF_3$—$(CF_2)_n$—$CH(CH_3)$—$(CH_2)_m$—$CH_3$ wherein n is an integer selected from 3 to 5 and m is an integer selected from 1 to 5 in the mixture, it may also be feasible to adapt the composition to the requirements of the intended ophthalmic use, for instance adapting to a patient with altered tear fluid composition and refractive index due to an eye condition and/or age.

Ex vivo Eye Irritation Test (EVEIT)

A comparison in respect of corneal healing process was conducted for two compositions comprising $CF_3(CF_2)_5(CH_2)_7CH_3$, namely compositions consisting of a mixture of the semifluorinated alkane $CF_3(CF_2)_5(CH_2)_7CH_3$ and $CF_3(CF_2)_5$—$CH(CH_3)$—$(CH_2)_5$—$CH_3$ (Composition A with 0.17 wt. % of $CF_3(CF_2)_5$—$CH(CH_3)$—$(CH_2)_5$—$CH_3$ and Composition B, with 64 wt. % of $CF_3(CF_2)_5$—$CH(CH_3)$—$(CH_2)_5$—$CH_3$) with hyaluronic acid (HYLO-COMOD®) as a reference and 0.01% BAC (benzalkonium chloride) as a positive control using an Ex Vivo Eye Irritation Test (EVEIT), similar to as described in M. Frentz et al, Altern. to Lab. Anim., 2008 (36) p 25-32; and N. Schrage et al, Graefes Arch Clin Exp Ophthalmol 2012 (250), 1330-1340).

Method. Rabbit corneas were obtained and placed in an artificial anterior ocular chamber which was gently filled with serum-free minimal essential medium (Eagle's MEM) containing Earle's salts and HEPES buffer for nutrition. The medium was constantly replenished by a micropump to imitate the physiological condition of the eye. The culture chambers were held at 32° C. under normal air without supplementary $CO_2$ and >95% relative humidity. Five corneas per test substance (n=5) were used except for the positive control with which two corneas (n=2) were tested.

After 12 h of stabilization in the culture chamber, the corneas were evaluated by microscopy and corneas with intact epithelium and without opacities were selected. Four small abrasions (2.3-4.3 mm²) were applied to the surface of the selected corneas with a cornea drill. All defects were monitored by fluorescein sodium staining (0.17% aq. solution) and microscopy.

The test substances were administered one hour after induction of the corneal erosion and were applied six times daily onto the apex of the corneas (30-50 μL every four hours). A soft-tipped cannula, with continuous suction was placed on the lowest part of the corneoscleral region within the culturing chamber to remove any excess fluid. Experiments were terminated after 3 days of application. Biomicroscopic images of the corneas were taken daily to document the corneal healing process using a phase-contrast microscope integrated camera (KY-F1030U, JVC, (Bad Vilbel, Del.) mounted on a Z16 APO Microscope (Wetzlar, Del.)). All defects were monitored by fluorescein sodium stains (0.17% aq. solution) with yellow green fluorescence indicating the areas of epithelial defects. Erosion sizes were determined using a software tool of the microscope (DISKUS). At the end of the 3 days, the experiment was terminated and all corneas were fixed in 3.7% formaldehyde and stained with a hematoxylin-eosin dye for microscopic evaluation. To monitor the metabolic activity of the cornea, glucose and lactate concentrations were photometrically quantified in the outflow medium from the artificial anterior chambers.

Results. Both mixtures of the semifluorinated alkanes (Composition A and B as referenced above) were observed to have a similar positive effect in respect of the corneal healing process after the induction of corneal erosion as compared with the standard reference hyaluronic acid composition (HYLO-COMOD®).

Corneal Erosion Size Measurements/Mean mm² (SD)

| Composition | Day 0 | Day 1 | Day 2 | Day 3 |
| --- | --- | --- | --- | --- |
| A (n = 5) | 12.8 (0.98) | 3.018 (0.89) | 0 (0) | 0 (0) |
| B (n = 5) | 12.23 (1.46) | 3.59 (0.53) | 0 (0) | 0 (0) |
| HYLO COMOD ® | 12.13 (1.29) | 3.11 (0.76) | 0.01 (0.02) | 0 (0) |
| 0.01% BAC | 11.57 (0.86) | 5.91 (0.28) | 8.74 (7.6) | 17.46 (6.43) |

Day 3 Histological Observations

| Composition | |
| --- | --- |
| A (n = 5) | Multilayered epithelium and dense stroma in all corneas. Keratocytes are well formed and arranged except if lost from initial erosion area. Descemet membrane appears intact, endothelial cells are present. |
| B (n = 5) | Healed epithelial layer with closed multilayer of epithelial cells. Dense stroma and regular formed keratocytes although typically reduced in number under the initial erosion area. Descemet membrane and endothelial layer present without structural defects |
| Hylo Comod ® (reference) | Multilayered epithelium and dense stroma with regular arranged and formed keratocytes except under the initial erosion areas where keratocytes are totally lost in the upper stroma. Descemet membrane and endothelial layer are present without any defects in structure. |
| 0.01% BAC (positive control) | Severe alterations of the superficial cornea with disintegration of whole corneal structures; observation of distinct edema Reduced staining of background substance indicating chemical alteration of collagen Severe reduction in number of keratocyte cells which also appear rounded and pycnotic. Descemet membrane is present with intact endothelium |

No significant differences in terms of a positive corneal healing was noted between composition B comprising 64 wt. %, based on total weight of the composition of semifluorinated alkane $CF_3(CF_2)_5$—$CH(CH_3)$—$(CH_2)_5$—$CH_3$ and composition A. With both compositions, as with the reference composition, the mechanically induced epithelial erosions were found to be significantly reduced and essentially absent after day 2 of treatment. FIG. 3 depicts the corneal erosion size measurements of the tested compositions, reference and positive controls for days 0-3 of the EVEIT experiment.

As noted in the table above, microscopic histological examination of the cross-sections of the corneas after termination of the experiment on day 3 revealed no significant remaining defects or differences in the corneas treated with compositions A, B and the reference HYLO-COMOD®.

Furthermore, no corneal toxicity, based on the metabolic activity as indicated by the glucose/lactate measurements was observed for these compositions.

In significant contrast, the positive control comprising 0.01% of the preservative BAC, a progressive increase of the induced epithelial lesions was observed over the course of the three days of the experiment.

The invention claimed is:

1. An ophthalmic composition comprising $CF_3$—$(CF_2)_3$—$CH(CH_3)$—$(CH_2)_2$—$CH_3$ and $CF_3$—$(CF_2)_3$—$(CH_2)_4$—$CH_3$.

2. The composition according to claim 1, wherein the composition consists of the $CF_3$—$(CF_2)_3$—$CH(CH_3)$—$(CH_2)_2$—$CH_3$ and the $CF_3$—$(CF_2)_3$—$(CH_2)_4$—$CH_3$.

3. The composition according to claim 1, being in liquid form and comprising at least 1 wt % of said compound $CF_3$—$(CF_2)_3$—$CH(CH_3)$—$(CH_2)_2$—$CH_3$ or from 1 wt % to 5 wt % of said compound $CF_3$—$(CF_2)_3$—$CH(CH_3)$—$(CH_2)_2$—$CH_3$, based on the total weight of the composition.

4. The composition according to claim 1, being formulated as a clear liquid solution.

5. The composition according to claim 1 being substantially free of:
(a) a polymer,
(b) a perfluorinated compound, and/or
(c) a dissolved pharmacologically active ingredient which is not a semifluorinated alkane.

6. The composition of according to claim 1, wherein the composition is in liquid form and consists essentially of the compound $CF_3$—$(CF_2)_3$—$CH(CH_3)$—$(CH_2)_2$—$CH_3$ in an amount from 1 wt % to 5 wt % and the compound $CF_3$—$(CF_2)_3$—$(CH_2)_4$—$CH_3$ in an amount up to 95 wt %, based on the total weight of the composition.

7. The composition according to claim 1, being in liquid form and comprising from 1 wt % to 5 wt % of $CF_3$—$(CF_2)_3$—$CH(CH_3)$—$(CH_2)_2$—$CH_3$ and up to 95 wt % of $CF_3$—$(CF_2)_3$—$(CH_2)_4$—$CH_3$, based on the total weight of the composition.

8. The composition according to claim 7, being formulated as a clear liquid solution.

9. The composition according to claim 8 being substantially free of:
(a) a polymer,
(b) a perfluorinated compound, and/or
(c) a dissolved pharmacologically active ingredient which is not a semifluorinated alkane.

10. The composition of according to claim 9, wherein the composition consists essentially of the $CF_3$—$(CF_2)_3$—$CH(CH_3)$—$(CH_2)_2$—$CH_3$ and the $CF_3$—$(CF_2)_3$—$(CH_2)_4$—$CH_3$, and optionally one or more lipophilic liquid constituents.

11. A kit comprising an ophthalmic composition according to claim 1 and a container for holding the composition, wherein said container comprises a dropper which dispenses droplets having a volume of 8 to 15 µL topically to a lacrimal sac, lower eyelid, eye surface, or other ophthalmic tissue.

12. A method of treating a disease or condition of a patient in need of such treatment, comprising administering the composition according to claim 1 to the patient.

13. The method according to claim 12, wherein the disease or condition is dry eye disease (keratoconjunctivitis sicca) or a symptom or condition associated therewith; and/or Meibomian Gland Dysfunction (MGD), or a symptom or condition associated therewith.

14. The method according to claim 13, wherein the composition is topically administered into the lacrimal sac, into the lower eyelid, to an eye surface or to an ophthalmic tissue.

15. The method according to claim 12, wherein the disease or condition is corneal damage.

16. A method of treating a disease or condition of a patient in need of such treatment, comprising administering the composition according to claim 10 to the patient.

17. The method according to claim 16, wherein the disease or condition is dry eye disease (keratoconjunctivitis sicca) or a symptom or condition associated therewith; and/or Meibomian Gland Dysfunction (MGD), or a symptom or condition associated therewith.

18. The method according to claim 16, wherein the disease or condition is corneal damage.

* * * * *

UNITED STATES PATENT AND TRADEMARK OFFICE
CERTIFICATE OF CORRECTION

PATENT NO. : 11,154,513 B2  
APPLICATION NO. : 15/280411  
DATED : October 26, 2021  
INVENTOR(S) : Scherer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 782 days.

Signed and Sealed this
Eighteenth Day of February, 2025

Coke Morgan Stewart
*Acting Director of the United States Patent and Trademark Office*